US008062857B1

(12) United States Patent
Hess et al.

(10) Patent No.: US 8,062,857 B1
(45) Date of Patent: Nov. 22, 2011

(54) H-FABP AS EARLY PREDICTOR OF MYOCARDIAL INFARCTION

(75) Inventors: Georg Hess, Mainz (DE); Hendrik Huedig, Penzberg (DE); Rosemarie Kientsch-Engel, Feldafing (DE); Dietmar Zdunek, Tutzing (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 110 days.

(21) Appl. No.: 12/623,495

(22) Filed: Nov. 23, 2009

Related U.S. Application Data

(63) Continuation of application No. PCT/EP2008/056603, filed on May 29, 2008.

(30) Foreign Application Priority Data

May 29, 2007 (EP) ..................................... 07109141
Sep. 13, 2007 (EP) ..................................... 07116337

(51) Int. Cl.
*G01N 33/53* (2006.01)
*G01N 31/00* (2006.01)

(52) U.S. Cl. ............ 435/7.21; 435/7.1; 436/1; 436/501; 436/518; 424/9.1; 424/520; 422/50; 530/300; 530/350

(58) Field of Classification Search ........................ None
See application file for complete search history.

(56) References Cited

U.S. PATENT DOCUMENTS 5,744,305 A    4/1998 Fodor et al.
2003/0109420 A1    6/2003 Valkirs et al.

OTHER PUBLICATIONS

International Search Report issued Jul. 28, 2008 in PCT Application No. PCT/EP2008/056603.
International Preliminary Report on Patentability issued Jun. 19, 2009 in PCT Application No. PCT/EP2008/056603.
Alpert, Joseph S. et al., Myocardinal Infarction Redefined—A Concensus Document on The Joint European Society of Cardiology/American College of Cardiology Committee for the Redefinition of Myocardial Infarction, Journal of the American College of Cardiology, 2000, pp. 959-969, vol. 36. No. 3.
Anderson, Page A. W. et al., Molecular Basis of Human Cardiac Troponin T Isoforms Expressed in the Developing, Adult, and Failing Heart, Circulation Research, Apr. 1995, pp. 681-686, vol. 76, No. 4.
Brogan, Gerard X., Jr. et al., Evaluation of a New Rapid Quantitative Immunoassay for Serum Myoglobin Versus CK-MB for Ruling Out Acute Myocardial Infarction in the Emergency Department, Annals of Emergency Medicine, Oct. 1994, pp. 665-671, vol. 24, No. 4.
Ferrieres, Gaelle et al., Human cardiac troponin I: precise identification of antigenic epitopes and prediction of secondary structure, Clinical Chemistry, 1998, pp. 487-493, vol. 44, No. 3.
Ishii, Junnichi et al., Prognostic Value of Serum Concentration of Heart-Type Fatty Acid-Binding Protein Relative to Cardiac Troponin T on Admission in the Early Hours of Acute Coronary Syndrome, Clinical Chemistry, Aug. 2005, pp. 1397-1404, vol. 51, No. 8.
Lefevre, G. et al., Evaluation multicentrique du dosage semi-quantitatif de la h-FABP (Cardio Detect(R)) au laboratoire central: interet dans le diagnostic de l'infarctus du myocarde, Annales de Biologie Clinique, Jul.-Aug. 2007, pp. 377-384, vol. 65, No. 4 (Abstract).
McCord, James et al., Ninety-Minute Exclusion of Acute Myocardial Infarction by Use of Quantitative Point-of-Care Testing of Myoglobin and Troponin I, Circulation, Sep. 25, 2001, pp. 1483-1488, vol. 104.
Morrow, David A. et al., Ability of Minor Elevations of Troponins I and T to Predict Benefit From an Early Invasive Strategy in Patients With Unstable Angina and Non-ST Elevation Myocardial Infarction Results From a Randomized Trial, Journal of the American Medical Association, Nov. 21, 2001, pp. 2405-2412, vol. 286, No. 19.
Morrow, David A. et al., National Academy of Clinical Biochemistry Laboratory Medicine Practice Guidelines: Clinical Characteristics and Utilization of Biochemical Markers in Acute Coronary Syndromes, Circulation, Apr. 3, 2007, pp. 356-375, vol. 115.
Needleman, Saul B. and Wunsch, Christian D., A General Method Applicable to the Search for Similarities in the Amino Acid Sequence of Two Proteins, Journal of Molecular Biology, 1970, pp. 443-453, vol. 48.
O'Donoghue, Michelle et al., Prognostic Utility of Heart-Type Fatty Acid Binding Protein in Patients With Acute Coronary Syndromes, Circulation, 2006, pp. 550-557, vol. 114.
Okamoto, Fumio et al., Human Heart-Type Cytoplasmic Fatty Acid-Binding Protein (H-FABP) for the Diagnosis of Acute Myocardial Infarction. Clinical Evaluation of H-FABP in Comparison with Myoglobin and Creatine Kinase Isoenzyme MB, Clin Chem Lab Med, 2000, pp. 231-238, vol. 38, No. 3.
Ordway, George A. and Garry, Daniel J., Myoglobin: an essential hemoprotein in striated muscle, The Journal of Experimental Biology, 2004, pp. 3441-3446, vol. 207.
Pearson, William R. and Lipman, David J., Improved tools for biological sequence comparison, Proceedings of the National Academy of Science USA, Apr. 1988, pp. 2444-2448, vol. 85.
Ruzgar, Ozcan et al., The use of human heart-type fatty acid-binding protein as an early diagnosis biochemical marker of myocardial necrosis in patients with acute coronary syndrome, and its comparison with troponin-T and creatine kinase-myocardial band, Heart Vessels, 2006, pp. 309-314, vol. 21.
Seino, Yoshihiko et al., Use of a Whole Blood Rapid Panel Test for Heart-Type Fatty Acid-Binding Protein in Patients with Acute Chest Pain: Comparison with Rapid Troponin T and Myoglobin Tests, American Journal of Medicine, Aug. 15, 2003, pp. 185-190, vol. 115, No. 3.
Smith, Temple F. and Waterman, Michael S., Comparison of Biosequences, Advances in Applied Mathematics, 1981, pp. 482-489, vol. 2.

(Continued)

*Primary Examiner* — Lisa Cook

(57) ABSTRACT

The present invention relates to a method for diagnosing myocardial infarction in a subject who suffers from acute coronary syndrome and has a cardiac troponin level which is detectable but lower than the level that is considered as being indicative for a myocardial infarction. Moreover, the present invention relates to a method for identifying a subject being susceptible to cardiac intervention, wherein the subject suffers from acute coronary syndrome and has a cardiac troponin level which is detectable but lower than a level that is considered as being indicative for a myocardial infarction. The methods of the present invention are based on the determination of H-FABP and, optionally, myoglobin in a sample of the subject and comparing the amount of H-FABP and, optionally, myoglobin to reference amounts.

13 Claims, 2 Drawing Sheets

OTHER PUBLICATIONS

Suzuki, Masaru et al., Prognostic Value of a Qualitative Test for Heart-Type Fatty Acid-Binding Protein in Patients With Acute Coronary Syndrome, International Heart Journal, Jul. 2005, pp. 601-606, vol. 46, No. 4.

Tanaka, Takao et al., Serum and Urinary Human Heart Fatty Acid-Binding Protein in Acute Myocardial Infarction, Clinicial Biochemistry, Apr. 1991, pp. 195-201, vol. 24.

Watanabe, Toshio et al., Development of a simple whole blood panel test for detection of human heart-type fatty acid-binding protein, Clinical Biochemistry, Jun. 2001, pp. 257-263, vol. 34, No. 4.

Wodzig, K. Will H. et al, One-step enzyme-linked immunosorbent assay (ELISA) for plasma fatty acid-binding protein, Annals of Clinicial Biochemistry, 1997, pp. 263-268, vol. 34, No. 3, British Medical Association, London, GB.

H-FABP AS EARLY PREDICTOR OF MYOCARDIAL INFARCTION

RELATED APPLICATIONS

This application is a continuation of PCT/EP2008/056603 filed May 29, 2008 and claims priority to EP 07116337.2 filed Sep. 13, 2007 and EP 07109141.7 filed May 29, 2007.

FIELD OF THE INVENTION

The present invention relates to a method for diagnosing myocardial infarction in a subject who suffers from acute coronary syndrome and has a cardiac troponin level, which is detectable, but lower than the level that is considered as being indicative for a myocardial infarction. Moreover, the present invention relates to a method for identifying a subject being susceptible to cardiac intervention, wherein the subject suffers from acute coronary syndrome and has a cardiac troponin level which is detectable, but lower than a level that is considered as being indicative for a myocardial infarction. The methods of the present invention are based on the determination of heart-type fatty acid binding protein (H-FABP) and, optionally, myoglobin in a sample of said subject and comparing the amount of heart-type fatty acid binding protein (H-FABP) and, optionally, myoglobin to at least one reference amount. Also comprised by the present invention are kits or devices to carry out the methods of the present invention.

BACKGROUND

An aim of modern medicine is to provide personalized or individualized treatment regimens. Those are treatment regimens which take into account a patient's individual needs or risks. A particularly important risk is the presence of cardiovascular complication, especially of an acute cardiovascular event. Cardiovascular complications belong to the leading causes of morbidity and mortality in the Western hemisphere. For individual treatment of a person who suffers from a cardiovascular complication, a reliable diagnosis has a significant impact on the success of the treatment of said person. This is particularly important for patients showing symptoms of acute coronary syndrome (ACS).

Acute coronary syndrome refers to a constellation of clinical symptoms caused by acute myocardial ischemia. Patients with acute coronary syndrome have a significantly increased risk of cardiac death and, therefore, need to be identified between the patients with nontraumatic chest symptoms (Morrow et al., National academy of clinical biochemistry guidelines: Clinical characteristics and utilization of biochemical markers in acute coronary syndrome, 2007, Circulation; 115;356-375). Patients exhibiting symptoms of an acute cardiovascular event (e.g., chest discomfort for more than 20 min) and presenting for emergency evaluation are generally examined by electrocardiography. Moreover, a blood sample is obtained for determining the level of a cardiac troponin. Cardiac troponin, e.g., troponin T, is a biomarker for myocardial infarction (MI). The electrocardiogram (ECG) provides important information for the diagnosis. Particularly, if the ECG shows elevated ST segments, a ST elevated myocardial infarction (STEM) is diagnosed. If the ECG does not show elevated ST segments, a non ST elevated MI (NSTEMI) is diagnosed when cardiac troponin is detected in a sample of the respective patient. Patients without a diagnostic ECG and with no detectable cardiac troponin are suspected to have unstable angina pectoris (UAP). Unstable angina and NSTEMI are considered to be closely related conditions, sharing a similar clinical presentation. However, they differ in their severity. NSTEMI is distinguished from unstable angina by ischemia causing irreversible myocardial damage which is detectable by biomarkers of myocardial necrosis (Morrow et al., loc. cit.). In all described cases, thus STEMI, NSTEMI and UAP, the patient is treated according to the diagnosis.

Within the last two decades biomarkers like cardiac troponin have become valuable tools for the diagnosis of heart-associated diseases. Further markers of heart-associated diseases are, e.g., NTproBNP, or creatine kinase isoenzyme MB (CK-MB). Recently, it was shown that the determination of myoglobin is a valuable tool for the diagnosis of subjects showing symptoms of ACS (Brogan G. X et al. Evaluation of a new rapid quantitative immunoassay for serum myoglobin versus CK-MB for ruling out acute myocardial infarction in the emergency department. 1994, Ann. Emerg. Med. 24(4): 665-71). The determination of myoglobin is advantageous because elevated concentrations can be determined shortly after the onset of symptoms (appr. 1 hour), and studies have demonstrated its high sensitivity for detection of AMI within the first few hours of ACS. However, the use of myoglobin for the diagnosis of myocardial infarctions has some limitations. Although the concentration of myoglobin rises quickly after the onset of symptoms, the concentration drops quickly after approximately 8 to 16 hours (James McCord J. at al. Ninety-Minute Exclusion of Acute Myocardial Infarction By Use of Quantitative Point-of-Care Testing of Myoglobin and troponin I. 2001, Circulation 104:1483; Morrow D. A. et al. National Academy of Clinical Biochemistry Laboratory Medicine Practice Guidelines: Clinical Characteristics and Utilization of Biochemical Markers in Acute Coronary Syndromes. 2007, Circulation, 115:356-375).

More recently, heart-type fatty acid binding protein (H-FABP) was suggested as an early marker of myocardial infarction. Heart-type fatty acid-binding protein (H-FABP) is a low molecular weight cytoplasmic protein and present abundantly in the myocardium. When the myocardium is injured, as in the case of myocardial infarction, low molecular weight cytoplasmic proteins including H-FABP are released into the circulation and an elevated H-FABP level is detectable in a blood sample. (e.g., Okamoto et al., Clin Chem Lab Med 38(3):231-8 (2000) Human heart-type cytoplasmic fatty acid-binding protein (H-FABP) for the diagnosis Of acute myocardial infarction. Clinical evaluation of H-FABP in comparison with myoglobin and creatine kinase isoenzyme MB; O'Donoghue et al., Circulation, 114;550-557 (2006) Prognostic Utility of Heart-Type Fatty Acid Binding Protein in patients with acute coronary syndrome or Ruzgar et al., Heart Vessels, 21;209-314 (2006) The use of human heart-type fatty acid-binding protein as an early diagnostic marker of myocardial necrosis in patients with acute coronary syndrome, and its comparison with troponin-T and its creatine kinase-myocardial band).

The finding that cardiac troponin, e.g., cardiac troponin T (TnT) or cardiac troponin I (TnI), is a marker of myocardial infarction has revolutionized the diagnosis and management of patients showing symptoms of ACS. Particularly, cardiac troponin T is a very specific marker of damage of the myocardium and, therefore, allows differentiating between UAP and MI in patients exhibiting symptoms of ACS. However, there are still some problems related to the use of cardiac troponin as a diagnostic marker in patients with acute coronary syndrome. E.g, the cardiac troponin level is generally not elevated at the onset of the symptoms of an acute coronary event. Generally, an elevated troponin level can be detected approximately 4 to 6 hours after the onset of symptoms of ACS. Thus, within the first 0 to 6 hours of an acute cardiovascular event, the use of troponin as a biomarker for the diagnosis of myocardial infarction causes a relatively high proportion of false negative results. Thus, a myocardial infarction might not be recognized by means of a cardiac troponin assay and this may result in a possibly inappropriate or delayed treatment. The introduction of a new generation of cardiac troponin tests, which are more sensitive than troponin tests of the previous generations and, thus, can detect much lower cardiac troponin levels, had enabled a more reliable and earlier detection of elevated cardiac troponin levels. Thus, in case of a myocardial event a necrosis may be detected earlier. However, recent studies brought evidence that, when using more sensitive troponin tests, cardiac troponin can also be reproducibly detected in patients with a stable coronary heart disease who do not suffer from an acute event (unpublished data). Thus, if a person with a stable coronary heart disease and an already elevated, but still low cardiac troponin level shows symptoms of ACS, it is unclear whether the detectable elevated cardiac troponin level is due to the acute event or due to the already existing coronary heart disease. This raises the possibility of an incorrect diagnosis, e.g., MI instead of UAP, resulting in a possibly harmful, wrong and/or delayed treatment.

Therefore, there is a clear need for diagnostic and prognostic means and methods allowing a reliable and quick diagnosis of. MI in a subject who shows symptoms of an acute coronary syndrome and who has a cardiac troponin level which is close to the detection limit. The said means and methods shall allow a diagnosis of said subject and shall allow identifying a subject being susceptible to cardiac intervention, an appropriate treatment of said subject and shall avoid the drawbacks of the current techniques as laid out above.

Thus, the technical problem underlying the present invention must be seen as the provision of means and methods for complying with the aforementioned needs.

The technical problem is solved by the embodiments characterized in the claims and herein below.

SUMMARY OF THE INVENTION

Accordingly, the present invention relates to a method for diagnosing myocardial infarction in a subject who suffers from acute coronary syndrome and has a cardiac troponin level which is detectable, but lower than the level that is considered as being indicative for a myocardial infarction, comprising
  (a) determining the amount of heart-type fatty acid binding protein (H-FABP) in a sample of said subject,
  (b) comparing the amount of H-FABP as determined in step a) to at least one reference amount, and
  (c) diagnosing myocardial infarction based on the information obtained in steps a) and b)

In an embodiment of the aforementioned method of the present invention, additionally the amount of the myoglobin is determined in an additional step aa) in a sample of said subject and compared to at least one reference amount for myoglobin in an additional step bb). Accordingly, in step c'), myocardial infarction is diagnosed based on the determined amounts of myoglobin and H-FABP and the comparison of the amount of myoglobin to at least one reference amount for myoglobin and the comparison of the amount of H-FABP to at least one reference amount for H-FABP. Preferably, the determination of H-FABP is carried out before the determination of myoglobin, however it is also contemplated the determination is carried out in any order, i.e. simultaneously, or at first H-FABP and then myoglobin, or at first myoglobin and then H-FABP.

The method of the present invention, preferably, is an in vitro method. Moreover, it may comprise steps in addition to those explicitly mentioned above. For example, further steps may relate to sample pre-treatments or evaluation of the results obtained by the method. The method of the present invention may be also used for monitoring, confirmation, and subclassification of a diagnosis. The method may be carried out manually or assisted by automation. Preferably, step (a), (b) and/or (c) may in total or in part be assisted by automation, e.g., by a suitable robotic and sensory equipment for the determination in step (a) or a computer-implemented comparison in step (b).

ROC curve analysis was done to determine diagnostic accuracy by calculation of diagnostic sensitivity vs. (1-specificity) for a given diagnostic parameter (H-FABP) according clinical outcome (Non-Myocardial Infarction (MD-Converter vs. Myocardial Infarction (MI)-Converter). Included in this ROC curve are the data obtained for patients with stable coronary heart disease and ACS (see Examples). The cut-off score for the clinical outcome MI is 4950 pg/ml H-FABP. (ROC-AUC: Receiver operating characteristic-area under curve; C. O. cut-off).

Figure 2:
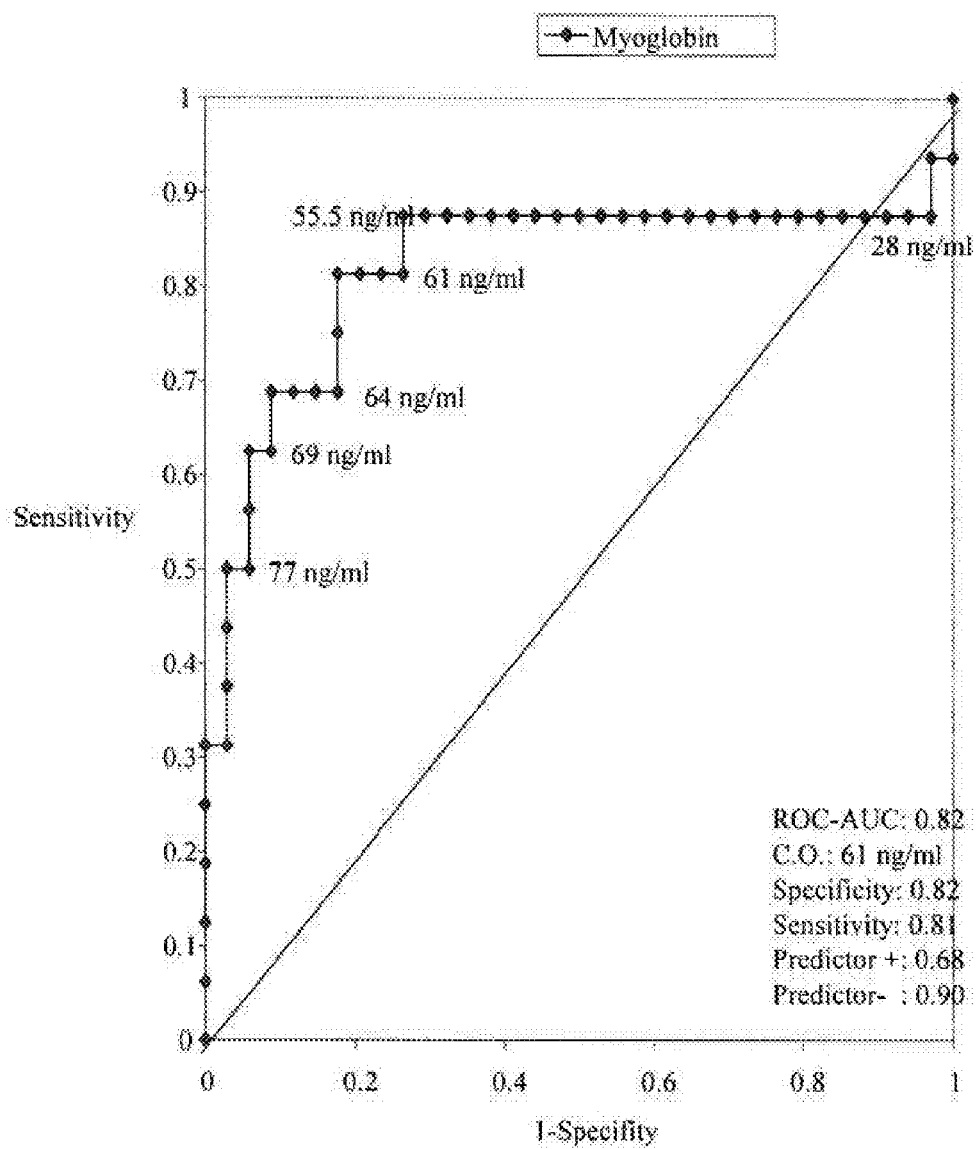

FIG. 2: Receiver operating characteristic (ROC) curve for myoglobin.

ROC curve analysis was done to determine diagnostic accuracy by calculation of diagnostic sensitivity vs. (1-specificity) for a given diagnostic parameter (myoglobin) according clinical outcome (Non-Myocardial Infarction (MI)-Converter vs. Myocardial. Infarction (MI)-Converter). Included in this ROC curve are the data obtained for patients with stable coronary heart disease and ACS (see Examples). The cut-off score for the clinical outcome MI is 61 ng/ml myoglobin. (ROC-AUC: Receiver operating characteristic-area under curve; C. O. cut-off).

DETAILED DESCRIPTION OF THE INVENTION

The term "diagnosing myocardial infarction" relates to assessing whether in a subject as defined in the present invention (thus a subject, who suffers from ACS and has a cardiac troponin level which is detectable but lower than the level that is considered as being indicative for MI) a myocardial infarction has recently occurred or not, and, thus, whether the underlying cause for an ACS is a myocardial infarction or unstable angina pectoris. The term "myocardial infarction" is known by the person skilled in the art. The term relates to the irreversible necrosis of the myocardium as a result of prolonged ischemia. As it will be understood by those skilled in the art, the diagnosis is usually not intended to be correct for 100% of the subjects to be analyzed. The term, however, requires that the diagnosis will be valid for a statistically significant portion of the subjects to be examined. Whether a portion is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983, Preferred confidence intervals are at least 90%, at least 95%, at least 97%, at least 98% or at least 99%. The p-values are, preferably, 0.1, 0.05, 0.01, 0.005, or 0.0001, Preferably, the probability envisaged by the present invention allows that the diagnosis will be correct for at least 60%, at least 70%, at least 80%, or at least 90% of the subjects of a given cohort.

The term "subject" as used herein relates to animals, preferably mammals, and, more preferably, humans.

The subject shall, preferably, show symptoms of ACS. The term "acute coronary syndrome" (ACS) is understood by the person skilled in the art. The term relates to a constellation of clinical symptoms caused by acute myocardial ischemia. The ischemia itself results from the disruption of an atherosclerotic plaque in a coronary artery. Symptoms for ACS, preferably, are chest pain for more than 20 minutes, shortness of breath, nausea, vomiting and or sweating. Moreover, it is known that the chest pain frequently radiates to the left arm and the left angle of the jaw. Generally, these clinical symptoms, especially chest pain, occur suddenly; they may appear at rest or after minimal exertion. Moreover, in the context of the present invention, the term "acute coronary syndrome" may also relate to suspected, assumed, or possible ACS, as these terms are frequently used for patients which show symptoms consistent with ACS, and but for which the diagnosis has not been conclusively established (see Morrow, loc. cit.). ACS patients can show unstable angina pectoris (UAP) or these individuals can suffer from a myocardial infarction (MI). MI can be an ST-elevated MI (STEMI) or a non-ST-elevated MI (NSTEMI). MI is classified as belonging to coronary heart diseases CHD and is preceded by other events also classified as belonging to CHD, like unstable angina pectoris UAP. Symptomatic for UAP is chest pain which is relieved by sublingual administration of nitroglycerine. UAP is caused by a partial occlusion of the coronary vessels leading to hypoxemia and myocardial ischemia. In case, the occlusion is too severe or total, an irreversible myocardial necrosis (which is the pathological state underlying myocardial infarction) results. Generally, STEMI is diagnosed by electrocardiography, in case the electrocardiogram (ECG) show ST-segment elevation. The determination of a cardiac troponin level at least six hours after the onset of symptoms of ACS allows for differentiating UAP and NSTEMI. If the troponin level is elevated (indicating myocardial damage) a NSTEMI is assumed. MI may occur without obvious symptoms, i.e. the subject does not show any discomfort, and the MI is not preceded by stable or unstable angina pectoris. The occurrence of an MI can be followed by a left ventricular dysfunction (LVD).

It is particularly contemplated that the subject shall suffer from coronary heart disease (frequently also referred to as coronary artery disease) prior to the ACS and already have detectable cardiac troponin levels at the onset of symptoms of ACS (and thus also prior to the onset of symptoms). Particularly, said subject shall have detectable levels of a cardiac troponin but lower than the level that is considered as being indicative for MI at the onset of symptoms of ACS. For said subject the method of the present invention will be particularly advantageous since, in case of an ACS, it is unclear whether elevated levels of a cardiac troponin indicate an acute event (ongoing necrosis) or are due to an already existing coronary heart disease.

The term "cardiac troponin" refers to all troponin isoforms expressed in cells of the heart and, preferably, the subendocardial cells. These isoforms are well characterized in the art as described, e.g., in Anderson 1995, Circulation Research, vol. 76, no. 4: 681-686 and Ferrieres 1998, Clinical Chemistry, 44: 487-493. Preferably, cardiac troponin refers to troponin T and/or troponin I, and, most preferably, to troponin T. It is to be understood that isoforms of Troponins may be determined in the method of the present invention together, i.e. simultaneously or sequentially, or individually, i.e. without determining the other isoform at all. Amino acid sequences for human troponin T and human troponin I are disclosed in Anderson, loc cit and Ferrieres 1998, Clinical Chemistry, 44: 487-493.

The term "cardiac troponin" encompasses also variants of the aforementioned specific Troponins, i.e., preferably, of troponin T (TnT) or troponin I (TnI). Such variants have at least the same essential biological and immunological properties as the specific cardiac Troponins. In particular, they share the same essential biological and immunological properties if they are detectable by the same specific assays referred to in this specification, e.g., by ELISA Assays using polyclonal or monoclonal antibodies specifically recognizing the said cardiac Troponins. Moreover, it is to be understood that a variant as referred to in accordance with the present invention shall have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino acid sequence of the specific troponin. Variants may be allelic variants or any other species specific homologs; paralogs, or orthologs. Moreover, the variants, referred to herein include fragments of the specific cardiac Troponins or the aforementioned types of variants as long as these fragments have the essential immunological and biological properties as referred to above. Such fragments may be, e.g., degradation products of the Troponins. Further included are variants which differ due to posttranslational modifications such as phosphorylation or myristylation.

The term "cardiac troponin level" as used herein relates to the concentration of a cardiac troponin, preferably of TnT. Preferably, the ternrrelates to the concentration of a cardiac troponin in a plasma or serum sample of a subject. The term "cardiac troponin level which is detectable" may relate to any cardiac troponin level which differs from zero and which is detectable by means and methods known the art, e.g., by commercially available cardiac troponin assays. Preferably, the "cardiac troponin level which is detectable" relates to a concentration that is equal or larger than the lowest detection limit of the assay used for determining the troponin level. Preferably, the troponin level which is detectable may relate to any concentration that is equal or larger than 0.001 ng/ml, 0.005 ng/ml, 0.0075 ng/ml, more preferably equal or larger than 0.01 ng/ml, or equal or larger than 0.002 ng/ml. Most preferably, the cardiac troponin level which is detectable relates to any concentration that is equal or larger than 0.002 ng/ml. It is to be understood that a detectable level (e.g., larger than 0.002 ng/ml) of a cardiac troponin is considered to be an elevated level of said cardiac troponin since such levels are usually not detected in healthy individuals. Moreover, an elevated level of a cardiac troponin indicates necrosis.

The term "troponin level which is considered as being indicative for myocardial infarction" relates to a commonly accepted troponin concentration that indicates a myocardial infarction. Preferably, the level considered as being indicative for myocardial infarction relates to a concentration that is above the 99th percentile concentration of a suitable reference population (cut-off score). This level is based upon a recommendation that was made by a joint committee of the European Society of Cardiology and the American College of Cardiology to avoid false positive results (The Joint European Society of Cardiology/American College of Cardiology Committee. Myocardial infarction redefined—a consensus document of the joint European Society of Cardiology/American College of Cardiology Committee for the Redefinition of Myocardial Infarction. J Am Coll Cardiol 2000;36: 959-969). The person skilled in the art knows how to select a suitable reference population and how to determine the 99th percentile concentration. It is to be understood that this concentration may differ based on the used assay for determining the cardiac troponin concentration and based on the selected reference population. Preferred cardiac troponin levels considered to be indicative for MI in the context of the present invention may be, but are not limited to 0.05 ng/ml, 0.075 ng/ml, 0.09.9 ng/ml, 0.1 ng/ml, 0.2 ng/ml and 0.3 ng/ml. The most preferred cardiac troponin level considered to be indicative for MI in the context of the present invention is 0.1 ng/ml.

In a preferred embodiment of the methods of the present invention, the troponin level, particularly the troponin T level, in a subject who suffers from acute coronary syndrome and has a cardiac troponin level which is detectable, but lower than the level that is considered as being indicative for a myocardial infarction (as defined in this application) ranges from 0.002 to 0.1 ng/ml (equal or larger than 0.002, but lower than 0.1 ng/ml).

Heart-type fatty acid binding protein, herein also referred to as H-FABP or heart fatty acid binding protein, is a small cytosolic protein that functions as the principal transporter of long-chain fatty acids in the cardiomyocyte. H-FABP is present in the myocardium and it is generally thought to be released rapidly into the circulation in response to myocardial injury. Several studies show that H-FABP is a early biochemical marker of myocardial infarction e.g., Okamoto et al., Clin Chem Lab Med 38(3):231-8 (2000) Human heart-type cytoplasmic fatty acid-binding protein (H-FABP) for the diagnosis of acute myocardial infarction. Clinical evaluation of H-FABP in comparison with myoglobin and creatine kinase isoenzyme MB; O'Donoghue et al., Circulation, 114;550-557 (2006) Prognostic Utility of Heart-Type Fatty Acid Binding Protein in patients with acute coronary syndrome or Ruzgar et al., Heart Vessels, 21;209-314 (2006) The use of human heart-type fatty acid-binding protein as an early diagnostic marker of myocardial necrosis in patients with acute coronary syndrome, and its comparison with troponin T and its creatine kinase-myocardial band).). H-FABP is well known in the art. Moreover, assays to determine the amount of H-FABP are also well known.

Myoglobin is a cytoplasmic hemoprotein consisting of a single polypeptide chain of 154 amino acids and is almost exclusively expressed solely in cardiac myocytes and oxidative skeletal muscle fibers. Like hemoglobin, myoglobin reversibly binds oxigen and thus may facilitate oxigen transport from red blood cells to mitochondria during periods of increased metabolic activity or serve as an oxigene reservoir during hypoxic or anoxic conditions Ordway G. and Garry D. J., Myoglobin: an essential hemoprotein in striated muscle. 2004, Journal of Experimental Biology 207, 3441-3446 (2004). Myoglobin is well known in the art. Moreover, assays to determine the amount of myoglobin are also well known.

Myoglobin and H-FABP as used herein encompass also variants of myoglobin and H-FABP polypeptides, respectively. Such variants have at least the same essential biological and immunological properties as the specific H-FABP and myoglobin polypeptides, respectively. In particular, they share the same essential biological and immunological properties if they are detectable by the same specific assays referred to in this specification, e.g., by ELISA assays using polyclonal or monoclonal antibodies specifically recognizing the said H-FABP and myoglobin polypeptides, respectively.

Moreover, it is to be understood that a variant as referred to in accordance with the present invention shall have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino sequence of the specific H-FABP and myoglobin polypeptides, respectively. The degree of identity between two amino acid sequences can be determined by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL, Math. 2:482 (1981), by the homology alignment algorithm of Needleman and Wunsch J. Mol. Biol. 48:443 (1970), by the search for similarity method of Pearson and Lipman Proc. Natl. Acad Sci. (USA) 85: 2444 (1988), by computerized implementations of these algorithms (GAP, BESTFIT, BLAST, PASTA, and TFASTA in the Wisconsin Genetics. Software Package, Genetics Computer Group (GCG), 575 Science Dr., Madison, Wis.), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Variants referred to above may be allelic variants or any other species specific homologs, paralogs, or orthologs. Moreover, the variants referred to herein include fragments of the specific H-FABP and myoglobin polypeptides, respectively or the aforementioned types of variants as long as these fragments have the essential immunological and biological properties as referred to above. Such fragments may be, e.g., degradation products of the H-FABP and myoglobin polypeptides, respectively. Further, included are variants which differ due to posttranslational modifications such as phosphorylation or myristylation.

The term "sample" refers to a sample of a body fluid, to a sample of separated cells or to a sample from a tissue or an organ. Samples of body fluids can be obtained by well known techniques and include, preferably, samples of blood, plasma, serum, or urine, more preferably, samples of blood, plasma or serum. Tissue or organ samples may be obtained from any tissue or organ by, e.g., biopsy. Separated cells may be obtained from the body fluids or the tissues or organs by separating techniques such as centrifugation or cell sorting. Preferably, cell-, tissue- or organ samples are obtained from those cells, tissues or organs which express or produce the peptides referred to herein. Preferably, the term "sample" refers to a plasma or serum sample, more preferably to a serum sample.

The sample is obtained at an appropriate time-point which is known by the skilled person. Preferably, the sample is obtained from a subject according the present invention shortly, preferably not more than 2 hours (and thus within 2 hours), and, more preferably, not more than 4 hours, and more preferably, not more than 6 hours after the onset of symptoms of acute coronary syndrome. The method of the present invention is particularly advantageous in cases the samples are obtained shortly after the onset of symptoms of ACS. In such cases it is unclear whether a detectable elevated cardiac troponin level is due to the acute event or due to the already existing coronary heart disease.

Determining the amount of H-FABP, preferably human H-FABP or myoglobin, preferably human myoglobin or any other peptide or polypeptide or protein referred to in this specification relates to measuring the amount or concentration, preferably semi-quantitatively or quantitatively. The terms polypeptide and protein are used interchangeable throughout this application. Measuring can be done directly or indirectly. Direct measuring relates to measuring the amount or concentration of the peptide or polypeptide based on a signal which is obtained from the peptide or polypeptide itself and the intensity of which directly correlates with the number of molecules, of the peptide present in the sample. Such a signal—sometimes referred to herein as intensity signal—may be obtained, e.g., by measuring an intensity value of a specific physical or chemical property of the peptide or polypeptide. Indirect measuring includes measuring of a signal obtained from a secondary component (i.e. a component not being the peptide or polypeptide itself) or a biological read out system, e.g., measurable cellular responses, ligands, labels, or enzymatic reaction products.

In accordance with the present invention, determining the amount of a peptide or polypeptide can be achieved by all known means for determining the amount of a peptide in a sample. Said means comprise immunoassay devices and methods which may utilize labeled molecules in various sandwich, competition, or other assay formats. Said assays will develop a signal which is indicative for the presence or absence of the peptide or polypeptide. Moreover, the signal strength can, preferably, be correlated directly or indirectly (e.g., reverse-proportional) to the amount of polypeptide present in a sample. Further suitable methods comprise measuring a physical or chemical property specific for the peptide or polypeptide such as its precise molecular mass or NMR spectrum. Said methods comprise, preferably, biosensors, optical devices coupled to immunoassays, biochips, analytical devices such as mass-spectrometers, NMR-analyzers, or chromatography devices. Further, methods include microplate ELISA-based methods, fully-automated or robotic immunoassays (available for example on ELECSYS analyzers), CBA (an enzymatic Cobalt Binding Assay, available for example on Roche-Hitachi analyzers), and latex agglutination assays (available for example on Roche-Hitachi analyzers).

Preferably, determining the amount of a peptide or polypeptide comprises the steps of (a) contacting a cell capable of eliciting a cellular response the intensity of which is indicative of the amount of the peptide or polypeptide with the said peptide or polypeptide for an adequate period of time, (b) measuring the cellular response. For measuring cellular responses, the sample or processed sample is, preferably, added to a cell culture and an internal or external cellular response is measured. The cellular response may include the measurable expression of a reporter gene or the secretion of a substance, e.g., a peptide, polypeptide, or a small molecule. The expression or substance shall generate an intensity signal which correlates to the amount of the peptide or polypeptide.

Also preferably, determining the amount of a peptide or polypeptide comprises the step of measuring a specific intensity signal obtainable from the peptide or polypeptide in the sample. As described above, such a signal may be the signal intensity observed at an m/z variable specific for the peptide or polypeptide observed in mass spectra or a NMR spectrum specific for the peptide or polypeptide.

Determining the amount of a peptide or polypeptide may, preferably, comprises the steps of (a) contacting the peptide with a specific ligand, (b) (optionally) removing non-bound ligand, (c) measuring the amount of bound ligand. The bound ligand will generate an intensity signal. Binding according to the present invention includes both covalent and non-covalent binding. A ligand according to the present invention can be any compound, e.g., a peptide, polypeptide, nucleic acid, or small molecule, binding to the peptide or polypeptide described herein. Preferred ligands include antibodies, nucleic acids, peptides or polypeptides such as receptors or binding partners for the peptide or polypeptide and fragments thereof comprising the binding domains for the peptides, and aptamers, e.g., nucleic acid or peptide aptamers. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g., phage display. Antibodies as referred to herein include both polyclonal and monoclonal antibodies, as well as fragments thereof, such as Fv, Fab and F(ab)2 fragments that are capable of binding antigen or hapten. The present invention also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the ligand or agent binds specifically to the peptide or polypeptide. Specific binding according to the present invention means that the ligand or agent should not bind substantially to ("cross-react" with) another peptide, polypeptide or substance present in the sample to be analyzed. Preferably, the specifically bound peptide or polypeptide should be bound with at least 3 times higher, more preferably at least 10 times higher and even more preferably at least 50 times higher affinity than any other relevant peptide or polypeptide. Non-specific binding may be tolerable, if it can still be distinguished and measured unequivocally, e.g., according to its size on a Western Blot, or by its relatively higher abundance in the sample. Binding of the ligand can be measured by any method known in the art. Preferably, said method is semi-quantitative or quantitative. Suitable methods are described in the following:

First, binding of a ligand may be measured directly, e.g., by NMR or surface plasmon resonance.

Second, if the ligand also serves as a substrate of an enzymatic activity of the peptide or polypeptide of interest, an enzymatic reaction product may be measured (e.g., the amount of a protease can be measured by measuring the amount of cleaved substrate, e.g., on a Western Blot). Alternatively, the ligand may exhibit enzymatic properties itself and the "ligand/peptide or polypeptide" complex or the ligand which was bound by the peptide or polypeptide, respectively, may be contacted with a suitable substrate allowing detection by the generation of an intensity signal. For measurement of enzymatic reaction products, preferably the amount of substrate is saturating. The substrate may also be labeled with a detectable lable prior to the reaction. Preferably, the sample is contacted with the substrate for an adequate period of time. An adequate period of time refers to the time necessary for a detectable, preferably measurable, amount of product to be produced. Instead of measuring the amount of product, the time necessary for appearance of a given (e.g., detectable) amount of product can be measured.

Third, the ligand may be coupled covalently or non-covalently to a label allowing detection and measurement of the ligand. Labeling may be done by direct or indirect methods. Direct labeling involves coupling of the label directly (covalently or non-covalently) to the ligand. Indirect labeling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.). The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g., magnetic beads", including paramagnetic and superparamagnetic labels), and fluorescent labels. Enzymatically active labels include e.g., horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-Star (Amersham Biosciences). ECF (Amersham Biosciences). A suitable enzyme-substrate combination may result in a colored reaction product, fluorescence or chemiluminescence, which can be measured according to methods known in the art (e.g., using a light-sensitive film or a suitable camera system). As for measuring the enyzmatic reaction, the criteria given above apply analogously. Typical fluorescent labels include fluorescent proteins (such as GFP and its derivatives), Cy3, Cy5, Texas Red, Fluorescein, and the Alexa dyes (e.g., Alexa 568). Further fluorescent labels are available e.g., from Molecular Probes (Oregon). Also the use of quantum dots as fluorescent labels is contemplated. Typical radioactive labels include 35S, 125I, 32P, 33P and the like. A radioactive label can be detected by any method known and appropriate, e.g., a light-sensitive film or a phosphor imager. Suitable measurement methods according the present invention also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA), scintillation, proximity assay (SPA), turbidimetry, nephelometry, latex-enhanced turbidimetry or nephelometry, or solid phase immune tests. Further methods known in the art (such as gel electrophoresis, 2D gel electrophoresis, SDS polyacrylamide gel electrophoresis (SDS-PAGE), Western Blotting, and mass spectrometry), can be used alone or in combination with labelling or other detection methods as described above.

The amount of a peptide or polypeptide may be, also preferably, determined as follows: (a) contacting a solid support comprising a ligand for the peptide or polypeptide as specified above with a sample comprising the peptide or polypeptide and (b) measuring the amount peptide or polypeptide which is bound to the support. The ligand, preferably chosen from the group consisting of nucleic acids, peptides, polypeptides, antibodies and aptamers, is preferably present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said ligand are well known and include, but are not limited to ionic, hydrophobic, covalent interactions and the like. It is also contemplated to use "suspension arrays" as arrays according to the present invention (Nolan 2002, Trends Biotechnol. 20(1):9-12). In such suspension arrays, the carrier, e.g., a microbead or microsphere, is present in suspension. The array consists of different microbeads or microspheres, possibly labeled, carrying different ligands. Methods of producing such arrays, for example based on solid-phase chemistry and photo-labile protective groups, are generally known (U.S. Pat. No. 5,744,305).

Preferably, the amount of the amount of H-FABP and the amount of myoglobin (if myoglobin is measured) are determined in a blood sample obtained from a subject as defined in the present invention. Preferably, such a determination is done by ELISA. Such a determination by ELISA can be done, e.g., by using the HBT ELISA Test Kit for human heart type fatty acid binding protein (HyCult Biotechnology, Uden, The Netherlands) for the determination of the amount of H-FABP and by using the Tina-Quant Myoglobin Test System (Roche Diagnostics) for the determination of the amount of myoglobin, respectively.

The term "amount" as used herein encompasses the absolute amount (e.g., of H-FABP or myoglobin), the relative amount or concentration (e.g., of H-FABP or myoglobin) as well as any value or parameter which correlates thereto. Such values or parameters comprise intensity signal values from all specific physical or chemical properties obtained from the said peptides by direct measurements, e.g., intensity values in mass spectra or NMR spectra. Moreover, encompassed are all values or parameters which are obtained by indirect measurements specified elsewhere in this description, e.g., expression levels determined from biological read out systems in response to the peptides or intensity signals obtained from specifically bound ligands. It is to be understood that values correlating to the aforementioned amounts or parameters can also be obtained by all standard mathematical operations.

The term "comparing" as used herein encompasses comparing the amount of the peptide, polypeptide, protein comprised by the sample to be analyzed with an amount of a suitable reference source specified elsewhere in this description. It is to be understood that comparing as used herein refers to a comparison of corresponding parameters or values, e.g., an absolute amount is compared to an absolute reference amount while a concentration is compared to a reference concentration or an intensity signal obtained from a test sample is compared to the same type of intensity signal of a reference sample. The comparison referred to in step (b) of the method of the present invention may be carried out manually or computer assisted. For a computer assisted comparison, the value of the determined amount may be compared to values corresponding to suitable references which are stored in a database by a computer program. The computer program may further evaluate the result of the comparison, i.e. automatically provide the desired assessment in a suitable output format. Based on the comparison of the amount(s) determined in step a) to suitable reference amount(s), it is possible to diagnose MI in said subject. It is to be understood that an amount of H-FABP as determined in step (a) of the methods of the presents invention is compared in step (b) to a reference amount for H-FABP as specified elsewhere in this application and that an amount of myoglobin is compared to a reference amount for myoglobin.

Accordingly, the term "reference amount" as used herein either refers to an amount which allows for ruling in a recent occurrence of MI or to an amount which allows for ruling out a recent occurrence of MI in a subject who suffers from acute coronary syndrome and has a cardiac troponin level which is detectable but lower than the level that is considered as being indicative for a myocardial infarction (thus in a subject as defined in the present invention). Recent occurrence in this context means that the MI has occurred, preferably, within a 6 hour period, more preferably within a 4 hour period, and most preferably within a 2 hour period before the sample was obtained from said subject. Preferably, a reference amount for ruling in MI may be derived from subject as defined in the present invention known to have suffered from a MI, preferably with within a 6 hour period, more preferably within a 4 hour period and most preferably within a 2 hour period before the sample was obtained. A reference amount for ruling out the recent occurrence of MI may be derived from a subject as defined in the present invention known to not have suffered from MI. Furthermore, a reference amount for ruling out the recent occurrence of a MI may be derived from a subject with stable coronary heart disease who has a low but detectable cardiac troponin level (as specified above) and who did not suffer from MI. An amount of H-FABP and an amount of myoglobin (in cases myoglobin is determined) in a subject as defined in the present invention of larger than the reference amount for ruling in the occurrence of MT shall be indicative for a recent occurrence of MI in said subject (and thus that the cause for the ACS is a MI). An amount of H-FABP and, if myoglobin is determined, an amount of myoglobin in a subject as defined in the present invention lower than the reference amount for ruling out the occurrence of MI shall be an indicator that a MI infarction has not occurred recently, thus said subject, preferably, suffers from UAP (and thus is an indicator that the cause for the ACS is UAP). It is to be understood in the context of the present invention that subjects as defined in the present invention whose H-FABP amount is between the above mentioned reference amounts (the reference amount for ruling in the recent occurrence of MI and the reference amount for ruling out the recent occurrence of MI) may be required to be diagnosed again. Preferably, this may be also done for the rare case in which both the amount of myoglobin and H-FABP are determined and in which the amounts do not correspond, e.g., one amount is larger (or lower) than the respective reference amount, whereas the other amount is not larger (or lower) than the respective reference amount. The new diagnosis, preferably, is done by determining the amount of the marker(s) and in a new, thus, later obtained sample of said subject. The new sample may be obtained from a subject; preferably, 1 hour, 2 hours, 3 hours after obtaining the first sample. In addition, myoglobin may be determined in said new sample. After obtaining the sample, the amount of H-FABP and of myoglobin can be determined in said new sample. Then, the thus obtained result(s) may be compared to reference amounts (as described elsewhere in this application). Preferably, the amount of a cardiac troponin is also determined in the sample and used for the diagnosis. Preferably, an amount of cardiac troponin T of larger than 0.1 ng/ml six hours after showing symptoms of ACS is indicative for MI.

The person skilled in the art knows how to determine a reference amount. It will be appreciated that the reference amount may also be chosen according to the desired sensitivity or a specificity of the diagnosis. Therefore, the reference amount may be chosen by the persons skilled in the art according to the desired sensitivity and specificity. Means for determining suitable reference amounts are known to the persons skilled in the art, e. g. a reference amount can be determined from Receiver-Operator-Curves (ROC) according to clinical studies.

A reference amount for H-FABP for ruling in the recent occurrence of MI in a subject as defined in the present invention defining a threshold amount for H-FABP is 4950 pg/ml, 5550 pg/ml or 6000 pg/ml or, more preferably, 5700 pg/ml.

An amount of H-FABP larger than the reference amount for H-FABP for ruling in the recent occurrence of MI is, more preferably, indicative for the recent occurrence of a MI, particularly a NSTEMI.

If in addition to H-FABP an amount of myoglobin is determined in a sample of a subject as defined in the present invention and compared to a reference amount, a reference amount for myoglobin for ruling in the recent occurrence of MI in a subject as defined in the present invention defining a threshold amount for myoglobin is 64 ng/ml, or 69 ng/ml and, more preferably, 77 ng/ml.

An amount of myoglobin larger than the reference amount for myoglobin for ruling in the recent occurrence of MI is, more preferably, indicative for the recent occurrence of a MI, particularly a NSTEMI, provided that also the amount of H-FABP in a sample of a subject is also larger than the reference amount for H-FABP for ruling in the recent occurrence of MI.

A reference amount for H-FABP for ruling out the recent occurrence of MI in a subject according to the present invention defining a threshold amount for H-FABP is 2100 pg/ml or 2300 pg/ml or, more preferably, 2500 pg/ml.

An amount of H-FABP lower than the reference amount for H-FABP for ruling out the recent occurrence is, more preferably, indicative that a myocardial infarction did not occur in a subject as defined in the present invention. Preferably, as a consequence the occurrence of a MI can be ruled out and, e.g., a UAP can be assumed.

If in addition to H-FABP an amount of myoglobin is determined in a sample of a subject as defined in the present invention and compared to a reference amount, a reference amount for myoglobin for ruling out the recent occurrence of MI in a subject according to the present invention defining a threshold amount for myoglobin is 28 ng/ml, or 61 ng/ml, or, more preferably, 55 ng/ml.

An amount of myoglobin lower than the reference amount for myoglobin for ruling out the recent occurrence of MI is, more preferably, indicative that a myocardial infarction did not occur in a subject as defined in the present invention, provided that that also the amount of H-FABP in a sample of a subject is also lower than the reference amount for H-FABP for ruling out the recent occurrence of MI. Preferably, as a consequence the occurrence of a MI can be ruled out and, e.g., a UAP can be assumed.

The term "at least one reference amount" means one or more than one reference amount, e.g., two reference amounts, e.g., the reference amount for ruling in the recent occurrence of MI and the reference amount for ruling out the recent occurrence of MI.

Figure 1:
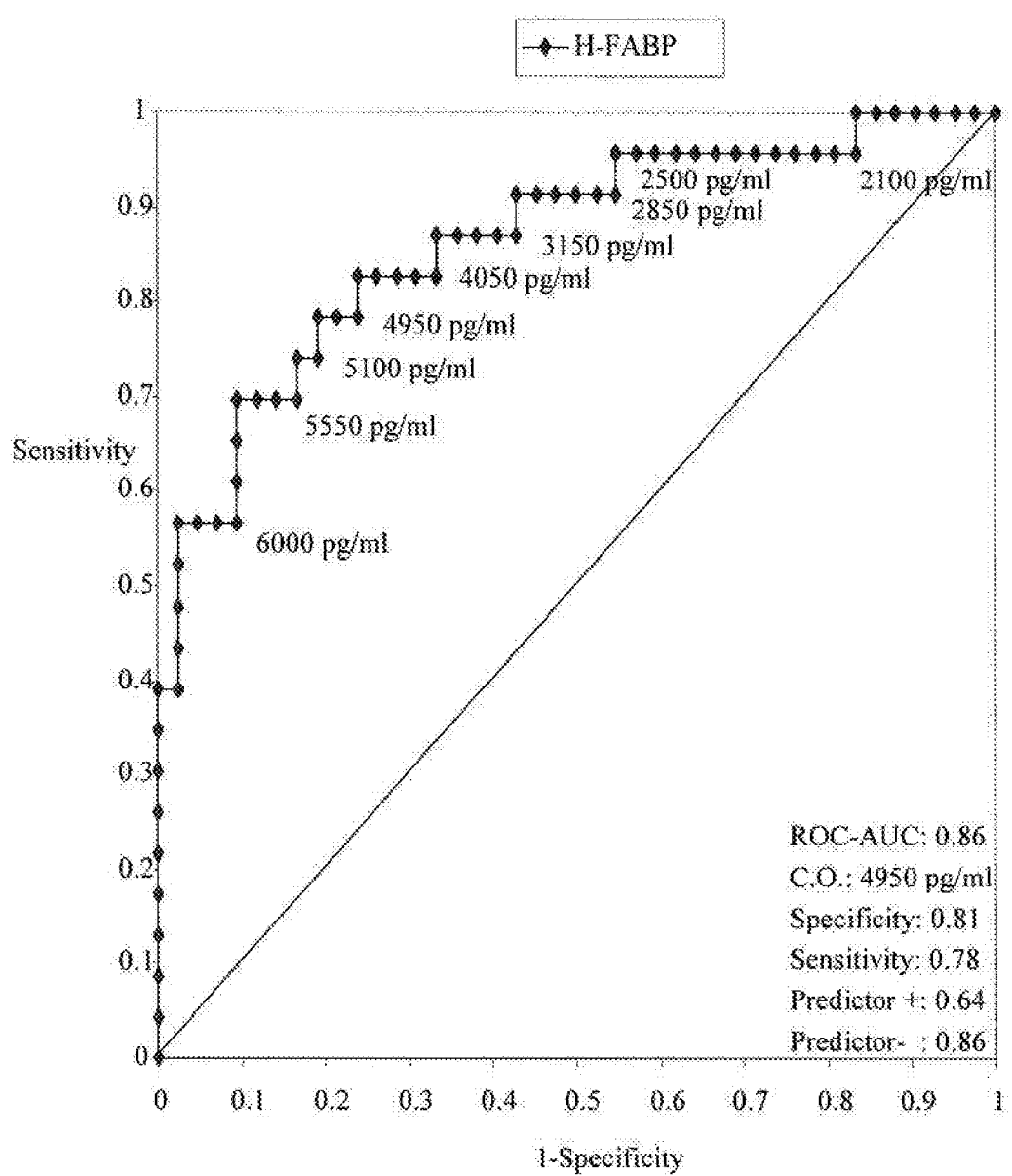
FIG. 1: Receiver operating characteristic (ROC) curve for H-FABP.

Advantageously, it has been found in the studies underlying the present invention that determining the amount of H-FABP in a subject as defined in the present invention (thus a subject suffering from acute coronary syndrome and having a troponin level which is detectable, but lower than the level considered as being indicative for MI) and comparing the determined amount to at least one reference amount is required for diagnosing MI in said subject. The aforementioned method is more reliable than those of the prior art since it has been found that H-FABP is required to assess the occurrence of a MI in case of low, but detectable cardiac troponin T levels shortly after the onset of symptoms of an ACS or assumed ACS. In the studies underlying the present invention, H-FABP levels and TnT levels were determined in patients showing symptoms of ACS (within the first 2 hours after the onset of symptoms). The TnT level was determined by using a highly sensitive troponin T assay with a detection limit of 0.002 ng/ml. Control experiments were carried out in which the amounts of TnT an H-FABP in patients with stable coronary disease were determined (i.e. in patients without an apparent acute event). These experiments showed that TnT can also be detected in subjects with stable coronary disease. A Receiver Operating Characteristic (ROC) curve analysis including the data of the aforementioned studies further illustrated that H-FABP is a strong biochemical marker for myocardial infarction (FIG. 1). Particularly, an H-FABP amount in a subject as defined in the present invention of larger than 5700 pg/ml indicates a recent occurrence of MI (rule in), whereas an amount of less than 2500 pg/ml indicates that a MI did not occur recently (rule out). Moreover, the sensitivity and specificity of a diagnosis based on the determination of H-FABP in a sample of a subject as defined in the present invention is even more increased when additionally the amount of myoglobin in a sample of a subject is determined and compared to reference amounts for myoglobin. Particularly, a myoglobin amount in a subject as defined in the present invention of larger than 77 ng/ml indicates a recent occurrence of MI (rule in), whereas an amount of less than 55 ng/ml indicates that a MI did not occur recently (rule out), FIG. 2. Thanks to this aspect of the present invention, a diagnosis for patients with ACS or assumed ACS with a low but detectable cardiac troponin level (detectable but lower than the level considered to be indicative for MI) can be more reliably performed. The findings of the study underlying the present invention may be particularly advantageous for the diagnosis of a) subjects who already have a low, but detectable, thus elevated levels of a cardiac troponin due to an already existing coronary heart disease and then shows symptoms of ACS and b) of subjects with ACS with a low, but detectable cardiac troponin level at the time at which the sample for the determination of the cardiac troponin level was obtained (e.g., because the sample was obtained too early) but in which a MI has recently occurred. In both cases, a) and b), the determination of H-FABP will be a valuable tool for the diagnosis, particularly for differentiating between UAP and MI. After diagnosis, the subject can be treated accordingly.

Without the determination of H-FABP, the diagnosis might be incorrect resulting in a putatively wrong, harmful and/or delayed treatment of the mentioned subjects. Moreover, the sensitivity and specificity of diagnosis can be even more enhanced when also myoglobin is determined.

In a preferred embodiment of the method of the present invention the method allows differentiating between myocardial infarction (MI) and unstable angina pectoris (UAP) in a subject who suffers from acute coronary syndrome and has a cardiac troponin level which is detectable, but lower than the level that is considered as being indicative for a myocardial infarction (MI).

Accordingly, the method of the present invention is, in an embodiment, a method for differentiating between myocardial infarction and unstable angina pectoris in a subject who suffers from acute coronary syndrome and has a cardiac troponin level which is detectable, but lower than the level that is considered as being indicative for a myocardial infarction (MI), comprising
  a) determining the amount of heart type fatty acid binding protein (H-FABP) in a sample of said subject, and
  b) comparing the amount of H-FABP determined in step a) to at least one reference amount, and
  c) differentiating between myocardial infarction and unstable angina pectoris based on the information obtained in steps a) and b).

It is particularly contemplated that the subject shall have low, but detectable levels of a cardiac troponin (thus, detectable but lower than the level that is considered as being indicative for MI) at the onset of symptoms of ACS (and, thus, shall have said have said levels prior to the ACS). Preferably, said detectable levels are due to a coronary heart disease. As mentioned above, in case of ACS it is difficult to decide whether the detectable levels are due to the existing coronary heart disease or due to the present ACS.

Therefore, in a preferred embodiment of the method of the present invention the method is for diagnosing myocardial infarction in a subject who suffers from acute coronary syndrome and has a cardiac troponin level which is detectable, but lower than the level that is considered as being indicative for a myocardial infarction (MI), and who had low, but detectable cardiac troponin levels already at the onset of symptoms of ACS.

Accordingly, the method of the present invention is, in an embodiment, a method for diagnosing myocardial infarction in a subject who suffers from acute coronary syndrome and has a cardiac troponin level which is detectable, but lower than the level that is considered as being indicative for a myocardial infarction (MI), and who had low, but detectable cardiac troponin levels already at the onset of symptoms of ACS, comprising the steps
  a) determining the amount of heart type fatty acid binding protein (H-FABP) in a sample of said subject, and
  b) comparing the amount of H-FABP determined in step a) to at least one reference amount, and
  c) diagnosing myocardial infarction based on the information obtained in steps a) and b).

In accordance with the foregoing, the present invention can also be used to rule in/rule out MI in a subject suffering from ACS.

Therefore, in another preferred embodiment of the method of the present invention the method is for ruling out myocardial infarction in a subject who suffers from acute coronary syndrome and has a cardiac troponin level which is detectable, but lower than the level that is considered as being indicative for a myocardial infarction (MI), and who had low, but detectable cardiac troponin levels already at the onset of symptoms of ACS (and, thus, also shortly before the onset of symptoms). Preferably, MI is ruled out if the level of H-FABP is lower than the reference amount for ruling out MI. If both H-FABP and myoglobin are determined, MI is ruled out if, preferably, if both markers are lower than the respective reference amount for ruling out MI.

Accordingly, the method of the present invention is, in an embodiment, a method for ruling out myocardial infarction in a subject who suffers from acute coronary syndrome and has a cardiac troponin level which is detectable, but lower than the level that is considered as being indicative for a myocardial infarction (MI), and who, preferably, had low, but detectable cardiac troponin levels already at the onset of symptoms of ACS comprising a) determining the amount of heart type fatty acid binding protein (H-FABP) in a sample of said subject, and
b) comparing the amount of H-FABP determined in step a) to a reference amount for ruling out myocardial infarction, and
c) ruling out myocardial infarction, if the amount of H-FABP is lower than the reference amount for ruling out myocardial infarction.

In another preferred embodiment of the method of the present invention the method is for ruling in myocardial infarction in a subject who suffers from acute coronary syndrome and has a cardiac troponin level which is detectable, but lower than the level that is considered as being indicative for a myocardial infarction (MI), and who, preferably, had low, but detectable cardiac troponin levels already at the onset of symptoms of ACS. Preferably, MI is ruled in if the level of H-FABP is larger than the reference amount for ruling in MI. If both H-FABP and myoglobin are determined, MI is ruled in, preferably, if both markers are larger than the respective reference amount for ruling in MI.

Explanations of the terms used for aforementioned methods can be found elsewhere herein. Preferably, they also comprise the determination of the amount of myoglobin and comparing said amount to a reference amount.

It is to be understood that according to the method of the present invention described herein above and below, the amount of H-FABP and, preferably, also myoglobin, or means for the determination thereof can be used for the manufacture of a diagnostic composition for diagnosing MI in a subject suffering from acute coronary syndrome and having a cardiac troponin level which is detectable but lower than the level considered as being indicative a myocardial infarction.

The present invention further relates to a method for identifying a subject being susceptible to cardiac intervention, whereby the subject suffers from acute coronary syndrome and has a cardiac troponin level which is detectable, but lower than a level that is considered as being indicative for a myocardial infarction, comprising carrying out the steps a) and b) and, optionally, steps aa) and bb) as laid out in any one of the aforementioned methods, and c) identifying a subject being susceptible to cardiac intervention.

Thanks to the aforementioned method, a risk/success stratification can be easily performed before subjecting a patient to a cardiac intervention. In case the patient turns out to be not susceptible for a cardiac intervention, said dangerous, time and/or cost intensive therapy can be avoided. Thus, besides preventing a subject from the adverse and severe side effects accompanying a cardiac intervention, the method of the present invention will be beneficial for the health system in that resources will be saved.

It is to be understood in the context of the aforementioned method of the present invention that a subject diagnosed to suffer from MI, thus a subject in which a MI has recently occurred, is susceptible to cardiac intervention.

The term "identifying" as used herein means assessing whether a subject will be susceptible for a cardiac intervention or not. As will be understood by those skilled in the art, such an assessment is usually not intended to be correct for all (i.e. 100%) of the subjects to be identified. The term, however, requires that a statistically significant portion of subjects can be identified (e.g., a cohort in a cohort study). Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983, Preferred confidence intervals are at least 90%, at least 95%, at least 97%, at least 98% or at least 99%. The p-values are, preferably, 0.1, 0.05, 0.01, 0.005, or 0.0001, More preferably, at least 60%, at, least 70%, at least 80% or at least 90% of the subjects of a population can be properly identified by the method of the present invention.

The term "cardiac intervention" encompasses those treatment regimens for MI considered appropriate by the person skilled in the art. The term comprises interventions by surgery, microsurgery, other invasive therapies affecting the cardiovascular system and, preferably, the heart, as well as conservative (non-surgery) methods of treatment. Conservative methods are known in the art and include non-pharmacological methods and pharmacological methods. Pharmacological methods relate to the administration of pharmaceuticals (such as heparin, acetylsalicylic acid, clopidogrel) in therapeutic effective amounts. Preferably, cardiac interventions as used herein are treatment regimens which aim to restore the proper oxygen supply of the heart. This is, preferably, achieved by restoring the blood flow throughout the blood vessels supporting the heart, i.e. the coronary blood vessels. Those blood vessels may be impaired due to, e.g., thrombotic or atherosclerotic plaques. Accordingly, cardiac interventions shall, preferably, comprise a destruction and/or removal of such plaques and a restoration of the vessel, if necessary. Preferred cardiac interventions in accordance with the present invention are selected from the group consisting of percutaneous coronary angioplasty, percutaneous transluminal coronary balloon angioplasty, laser angioplasty, coronary stent implantation, bypass implantation or intraluminal techniques aiming to restore blood flow, vessel patency, stabilize plaque, and/or reduce intracoronary thrombus load.

Moreover, the present invention relates to a method of deciding on the possible treatment of a subject who suffers from acute coronary syndrome and has a cardiac troponin level which is detectable, but lower than the level that is considered as being indicative for a myocardial infarction, comprising a) determining the amount of H-FABP in a sample of said subject, and
b) comparing the amount of H-FABP determined in step a) to at least one reference amount, and
c) recommending the initiation of a cardiac intervention or refraining from the cardiac intervention, based on the information obtained in steps a) and b).

In an embodiment of the aforementioned method of the present invention, additionally the amount of the myoglobin is determined step a) in a sample of a subject and compared to at least one reference amount for myoglobin in step b). Accordingly, in the step c) the recommendation of the initiation or cardiac intervention and or the refraining from a cardiac intervention is done based on the determined amounts of H-FABP and myoglobin, the comparison of the amount of myoglobin to at least one reference amount for myoglobin and the comparison of the amount of H-FABP to at least one reference amount for H-FABP.

Moreover, encompassed by the present invention is a kit or device for carrying out the methods of the present invention comprising means for determining the amount of H-FABP and in a sample of a subject and means for comparing said amount to at least one reference amount. Preferably, the kit or device also comprises means for determining the amount of myoglobin in a sample of a subject and means for comparing said amount to at least one reference amount.

The term "kit" as used herein refers to a collection of the aforementioned means, preferably, provided separately or within a single container. The kit may in addition comprise means for determining the amount of a cardiac troponin. Preferably, the kit may additionally comprise a user's manual for interpreting the results of any measurement(s) with respect to diagnosing MI in a subject as defined in the present invention. Particularly, such manual may include information about what determined amounts corresponds to what kind of diagnosis. This is outlined in detail elsewhere in this specification. Additionally, such user's manual may provide instructions about correctly using the components of the kit for determining the amount of the respective biomarkers.

The term "device" as used herein relates to a system of means comprising at least the aforementioned means operatively linked to each other as to allow the diagnosis of MI or the identification of a subject being susceptible to cardiac intervention. The device invention may in addition comprise means for determining the amount of a cardiac troponin. Preferred means for determining the amount or myoglobin and H-FABP and means for carrying out the comparison are disclosed above in connection with the method of the invention. How to link the means in an operating manner will depend on the type of means included into the device. For example, where means for automatically determining the amount of the peptides are applied, the data obtained by said automatically operating means can be processed by, e.g., a computer program in order to obtain the desired results. Preferably, the means are comprised by a single device in such a case. Said device may accordingly include an analyzing unit for the measurement of the amount of the peptides or polypeptides in an applied sample and a computer unit for processing the resulting data for the evaluation. Alternatively, where means such as test stripes are used for determining the amount of the peptides or polypeptides, the means for comparison may comprise control stripes or tables allocating the determined amount to a reference amount. The test stripes are, preferably, coupled to a ligand which specifically binds to the peptides or polypeptides referred to herein. The strip or device, preferably, comprises means for detection of the binding of said peptides or polypeptides to the said ligand. Preferred means for detection are disclosed in connection with embodiments relating to the method of the invention above. In such a case, the means are operatively linked in that the user of the system brings together the result of the determination of the amount and the diagnostic or prognostic value thereof due to the instructions and interpretations given in a manual. The means may appear as separate devices in such an embodiment and are, preferably, packaged together as a kit. The person skilled in the art will realize how to link the means without further ado. Preferred devices are those which can be applied without the particular knowledge of a specialized clinician, e.g., test stripes or electronic devices which merely require loading with a sample. The results may be given as output of raw data which need interpretation by the Clinician. Preferably, the output of the device is, however, processed, i.e. evaluated, raw data the interpretation of which does not require a clinician. Further preferred devices comprise the analyzing units/devices (e.g., biosensors, arrays, solid supports coupled to ligands specifically recognizing the myoglobin or H-FABP, Plasmon surface resonance devices, NMR spectrometers, mass-spectrometers etc.) or evaluation units/devices referred to above in accordance with the method of the invention.

The present invention also relates to the use of H-FABP and, preferably in addition, myoglobin and/or means for determining the amount of H-FABP and, preferably in addition, myoglobin and/or means for comparing the amount of H-FABP and, preferably in addition, myoglobin to at least one reference amount for the manufacture of a diagnostic composition for diagnosing myocardial infarction in a subject.

All references cited in this specification are herewith incorporated by reference with respect to their entire disclosure content and the disclosure content specifically mentioned in this specification.

The following Examples shall merely illustrate the invention. They shall not be construed, whatsoever, to limit the scope of the invention.

Example 1

Myoglobin, H-FABP and Troponin T in Patients with Acute Coronary Syndrome 69 patients showing characteristic symptoms of ACS (e.g., chest pain) were examined. Blood samples were obtained within the first two hours after the onset of symptoms. For the diagnosis of a ST-elevated MI patients were examined by electrocardiography. Additionally, the troponin T concentration was determined with a troponin T assay with a detection limit of 0.01 ng/ml. Further blood samples were obtained from patients for whom a diagnosis STEMI or NSTEMI could not be made (TnT concentration larger 0.01 but lower than 0.1 ng/ml, thus, levels which indicate necrosis). A troponin T level of larger than 0.1 ng/ml in a sample that was obtained at least 6 hours after the onset of symptoms was considered as being indicative for the recent occurrence MI (MI-converter), otherwise UAP was diagnosed (Non-MI-converter).

In a later analysis, the TnT, myoglobin and H-FABP concentration in samples from patients for whom a diagnosis of STEMI or NSTEMI could not be made (TnT in a first sample detectable, larger 0.01 ng/ml, but lower 0.1 ng/ml) were determined by using a highly-sensitive TnT assay with a detection limit of 0.002 ng/ml, TINA-QUANT Myoglobin Test System (Roche Diagnostics GmbH) and a H-FABP ELISA Test Kit, respectively (HBT ELISA Test kit for human heart type fatty acid binding protein; HyCult Biotechnology, Uden, The Netherlands). The results are shown in the following table.

TABLE troponin T, H-FABP and myoglobin concentrations (Medians) in patients with acute coronary syndrome (MI Converter and Non-MI Converter).

|  | High-Sensitive troponin T [pg/ml] | | Heart type-Fatty Acid Binding Protein [pg/ml] | | Myoglobin [ng/ml] | |
|---|---|---|---|---|---|---|
|  | Non-MI- | MI | Non-MI | MI | Non-MI | MI |
| N | 42 | 27 | 42 | 27 | 42 | 27 |
| Median | 4.35 | 22.75 | 2896.39 | 8114.01 | 36.89 | 76.76 |

Example 2

Myoglobin, H-FABP and Troponin T in Patients with Stable Coronary Heart Disease Myoglobin, H-FABP and sensitive troponin T were determined in blood samples of a total of 234 patients with stable coronary heart disease. The patients did not apparently suffer from an acute coronary event. H-FABP was determined as specified above. Troponin T was determined by a highly-sensitive troponin T test with a detection limit of 0.002 ng/ml. Patients were subjected to a detailed cardiologic investigation including echocardiography and coronary angioplasty. The coronary heart disease was subclassified into 1-, 2- or 3-vessel diseases, whereby stenosis of more than 50% should occur per vessel. The results are shown in the following tables.

TABLE

H-FABP quartiles in patients with documented stable coronary heart disease.

|  | H-FABP [pg/ml] N = 234 | | | |
|---|---|---|---|---|
|  | 1. Quartil | 2. Quartil | 3. Quartil | 4. Quartil |
| N | 60 | 55 | 59 | 60 |
| Median H-FABP pg/ml | 1132.1 | 1870.0 | 2636.5 | 4086.8 |
| Range | 0-1550 | 1565-2208 | 2223-3337 | 3357-46370 |
| Age, median | 61 | 64 | 66 | 71 |
| Coronary artery disease |  |  |  |  |
| 1-vessel disease | 22 | 9 | 10 | 10 |
| 2-vessel disease | 15 | 10 | 19 | 16 |
| 3-vessel disease | 15 | 25 | 23 | 29 |
| Median NT-proBNP pg/ml | 123.0 | 163.6 | 354.8 | 835.3 |
| Range | 11.2-35802 | 5.0-5514 | 6.9-13583 | 29.6-14953 |
| Median Hs-TnT ng/ml | 0.003 | 0.005 | 0.007 | 0.014 |
| Range | 0.0-0.113 | 0.0-0.553 | 0.0-0.600 | 0.0-0.708 |

TABLE

Myoglobin quartiles in patients with documented stable coronary heart disease.

|  | Myoglobin [ng/ml] N = 264 Diagnosis Group I: Stable coronary artery disease | | | |
|---|---|---|---|---|
|  | 1. Quartil | 2. Quartil | 3. Quartil | 4. Quartil |
| Median Myoglobin ng/ml | 22.87 | 29.22 | 37.74 | 48.84 |
| Range | 20.00-25.91 | 25.98-32.73 | 32.79-42.29 | 42.50-538.24 |
| Age, median | 67 | 65 | 67 | 65 |
| Coronary artery disease |  |  |  |  |
| 1-vessel disease | 22 | 20 | 28 | 28 |
| 2-vessel disease | 2 | 1 | 4 | 4 |
| 3-vessel disease | 0 | 0 | 0 | 0 |
| Median NT-proBNP pg/ml | 154.0 | 241.8 | 330.6 | 606.5 |
| Range | 17.7-35802 | 5.0-6431 | 6.9-14953 | 27.1-9582 |
| Median Hs-TnT ng/ml | 0.005 | 0.005 | 0.007 | 0.013 |
| Range | 0.0-0.600 | 0.0-0.553 | 0.0-0.500 | 0.0-0.708 |
| Median H-FABP pg/ml | 1518 | 1861 | 2498 | 3585 |
| Range | 3.5-7524 | 0.0-4463 | 742-6778 | 1933-46370 |

What is claimed is:

1. A method for diagnosing myocardial infarction in a subject, wherein the subject suffers from acute coronary syndrome (ACS) and has a cardiac troponin level which is detectable but lower than the level that is considered indicative for a myocardial infarction (MI), the method comprising:
   a) obtaining a sample from the subject,
   b) determining an amount of heart type fatty acid binding protein (H-FABP) in the sample,
   c) comparing the amount of H-FABP determined to a reference amount of H-FABP for ruling in a recent occurrence of MI and comparing the amount of H-FABP determined to a reference amount of H-FABP for ruling out a recent occurrence of MI, wherein
   an amount of H-FABP larger than the reference amount for ruling in a recent occurrence of MI is indicative for the recent occurrence of MI and an amount of H-FABP lower than the reference amount for ruling out a recent occurrence of MI is indicative that a MI has not occurred.

2. The method of claim 1 wherein the reference amount for ruling in a recent occurrence of MI is 5700 pg/ml.

3. The method of claim 1 wherein the reference amount for ruling out a recent occurrence of MI is 2500 pg/ml.

4. The method of claim 1, wherein the sample is obtained from the subject within 4 hours after onset of symptoms of ACS.

5. The method of claim 1 wherein the cardiac troponin is troponin T.

6. The method of claim 1 wherein the cardiac troponin level ranges from 0.002 ng/ml to 0.1 ng/ml.

7. A method for diagnosing myocardial infarction in a subject, wherein the subject suffers from acute coronary syndrome (ACS) and has a cardiac troponin level which is detectable but lower than the level that is considered indicative for a myocardial infarction (MI), the method comprising:
   a) obtaining a sample from the subject,
   b) determining an amount of heart type fatty acid binding protein (H-FABP) in the sample,
   c) determining an amount of myoglobin in the sample,
   d) comparing the amount of myoglobin determined and the amount of H-FABP determined to reference amounts of myoglobin and H-FABP, respectively, for ruling out a recent occurrence of myocardial infarction, and comparing the amount of myoglobin determined and the amount of H-FABP determined to reference amounts of myoglobin and H-FABP, respectively, for ruling in a recent occurrence of myocardial infarction,
   wherein a myoglobin amount and an H-FABP amount larger than the reference amounts of myoglobin and H-FABP for ruling in a recent occurrence of myocardial infarction is indicative for a recent occurrence of myocardial infarction, and a myoglobin amount and an H-FABP amount lower than the reference amounts of myoglobin and H-FABP for ruling out a recent occurrence of myocardial infarction is indicative that a myocardial infarction has not occurred.

8. The method of claim 7 wherein the reference amount of myoglobin for ruling in a recent occurrence of myocardial infarction is 77 ng/ml and the reference amount of FABP for ruling in a recent occurrence of myocardial infarction is 5700 pg/ml for H-FABP.

9. The method of claim 7 wherein the reference amount of myoglobin for ruling out a recent occurrence of myocardial infarction is 55 ng/ml and the reference amount of FABP for ruling out a recent occurrence of myocardial infarction is 2500 pg/ml for H-FABP.

10. A method for identifying a subject being susceptible to cardiac intervention, wherein the subject suffers from acute coronary syndrome (ACS) and has a cardiac troponin level which is detectable but lower than the level that is considered indicative for a myocardial infarction (MI), the method comprising:
    a) obtaining a sample from the subject,
    b) determining an amount of heart type fatty acid binding protein (H-FABP) in the sample,
    c) comparing the amount of H-FABP determined to a reference amount of H-FABP for ruling in a recent occurrence of MI and comparing the amount of H-FABP determined to a reference amount of H-FABP for ruling out a recent occurrence of MI, wherein
    an amount of H-FABP larger than the reference amount for ruling in a recent occurrence of MI is indicative for the recent occurrence of MI and an amount of H-FABP lower than the reference amount for ruling out a recent occurrence of MI is indicative that a MI has not occurred, thereby identifying whether the subject is susceptible to cardiac intervention.

11. A method of deciding on the possible treatment of a subject, wherein the subject suffers from acute coronary syndrome (ACS) and has a cardiac troponin level which is detectable but lower than the level that is considered indicative for a myocardial infarction (MI), the method comprising:
    a) obtaining a sample from the subject,
    b) determining an amount of heart type fatty acid binding protein (H-FABP) in the sample,
    c) comparing the amount of H-FABP determined to a reference amount of H-FABP for ruling in a recent occurrence of MI and comparing the amount of H-FABP determined to a reference amount of H-FABP for ruling out a recent occurrence of MI, wherein
    an amount of H-FABP larger than the reference amount for ruling in a recent occurrence of MI is indicative for the recent occurrence of MI and an amount of H-FABP lower than the reference amount for ruling out a recent occurrence of MI is indicative that a MI has not occurred, thereby permitting decision on possible treatment of the subject.

12. A method for ruling out myocardial infarction in a subject, wherein the subject suffers from acute coronary syndrome (ACS) and has a cardiac troponin level which is detectable but lower than the level that is considered indicative for a myocardial infarction (MI), the method comprising:
    a) obtaining a sample from the subject,
    b) determining an amount of heart type fatty acid binding protein (H-FABP) in the sample,
    c) comparing the amount of H-FABP determined to a reference amount of H-FABP for ruling out a recent occurrence of MI, wherein
    an amount of H-FABP lower than the reference amount for ruling out a recent occurrence of MI is indicative that a MI has not occurred, thereby permitting ruling out myocardial infarction in the subject.

13. The method of claim 12 wherein said subject already had a cardiac troponin level which is detectable, but lower than the level that is considered as being indicative for a myocardial infarction (MI) at the onset of symptoms of ACS.

* * * * *